US008690809B2

(12) United States Patent
Salas

(10) Patent No.: US 8,690,809 B2
(45) Date of Patent: Apr. 8, 2014

(54) HAND AND FOREARM ELEVATION DEVICE AND METHODS OF USE

(76) Inventor: Rafael Emerick Salas, Tampa, FL (US)

( * ) Notice: Subject to any disclaimer, the term of this patent is extended or adjusted under 35 U.S.C. 154(b) by 266 days.

(21) Appl. No.: 12/969,829

(22) Filed: Dec. 16, 2010

(65) Prior Publication Data

US 2012/0152259 A1 Jun. 21, 2012

(51) Int. Cl.
*A61F 5/00* (2006.01)

(52) U.S. Cl.
USPC .............................. 602/21; 128/845; 128/881

(58) Field of Classification Search
USPC .......... 602/20–23, 60–62; 128/878–879, 881; 5/624, 648, 650–651
See application file for complete search history.

(56) References Cited

U.S. PATENT DOCUMENTS 2,704,069 A * 3/1955 Donelan ...................... 128/881
RE32,680 E * 5/1988 Pompa ......................... 128/881
5,716,334 A * 2/1998 Wade ................................ 602/6
5,891,079 A * 4/1999 Barnes ............................ 602/61
6,061,854 A * 5/2000 Crowley ........................... 5/655
6,149,613 A * 11/2000 Klein .............................. 602/23
2003/0014820 A1* 1/2003 Fuhriman ......................... 5/646
2009/0119845 A1* 5/2009 Bastien et al. .................... 5/646

* cited by examiner

*Primary Examiner* — Michael A. Brown
(74) *Attorney, Agent, or Firm* — K&L Gates LLP

(57) ABSTRACT

A device for keeping a patient's forearm and hand substantially vertically elevated. The device includes a padded body having a base and a vertical supporting region defining a groove. The patient's forearm is positioned such that the forearm is suspended and supported in the groove of the padded body such that the elbow will rest lightly on the base of the padded body. A strap is attached to the vertical supporting region to secure the forearm. In another aspect, the invention relates to a method for using a device for keeping a patient's forearm and hand substantially vertically elevated. The method includes the steps of providing a padded body having a base and a vertical supporting region defining a groove and placing the forearm in the padded body such that the forearm is positioned and suspended into the groove and the elbow rests lightly on the base.

9 Claims, 8 Drawing Sheets

HAND AND FOREARM ELEVATION DEVICE AND METHODS OF USE

FIELD OF INVENTION

This invention relates generally to the field of medical devices, and more particularly medical devices for use by a patient who is required to keep his or her forearm and hand vertically oriented.

BACKGROUND

Medical devices exist to aid in supporting an injured arm, forearm, and/or hand of a patient during the course of or following treatment. Often the medical device used is a sling, which provides some support to protect the forearm and/or hand as it heals. Traditional slings are made of a soft fabric with a strap that attaches to one end of the cloth, wraps around the patient's shoulder, and attaches at the opposite end of the fabric. The fabric is constructed in such a way that the patient's forearm rests in a pouch with the patient's hand typically protruding from one end.

Such traditional slings, however, typically maintain the forearm in a generally horizontal position substantially parallel to ground level. Such a position is not beneficial to aid the recovery from an injury which requires elevation to promote drainage and healing. Furthermore, traditional slings do not permit solid stabilization of the forearm in a vertical position when the patient is seated. Finally such slings are uncomfortable for the patient putting additional stress on the upper arm.

Accordingly, there is a need for a medical device for use by a patient with a forearm and/or hand injury that comfortably stabilizes a patient's forearm and/or hand while facilitating drainage and healing.

SUMMARY OF INVENTION

In one aspect, the invention relates to a device for keeping a forearm and hand of a patient oriented in substantially a vertical direction. In one embodiment the device includes a padded body having a base and a vertical supporting region defining a groove in which said forearm is positioned such that the elbow of the forearm of the patient will rest lightly on the base of the padded body and the forearm will be suspended in the groove of the padded body. A strap is attached to the vertical supporting region, to secure and suspend the forearm in the device. In one embodiment the strap is made having a portion of Velcro. In another embodiment the padded body is enclosed by a removable cover having at least one opening into which the padded body is inserted. In another embodiment the padded body is lined with a liner or fabric, and the liner or fabric is secured to the padded body by Velcro or a snap or a clasp. In yet another embodiment, the base is substantially triangular or U-shaped, and the length of the vertical supporting region is substantially the length of the forearm of the patient. In still a further embodiment, the base is substantially flared to prevent forward rolling and backward rolling or lateral rolling, and the length of the vertical supporting region is substantially the length of the forearm of said patient.

In another aspect, the invention relates to a method for using a device for keeping a forearm of a patient oriented vertically. In one embodiment, the method comprises the steps of providing a padded body having a base and a vertical supporting region defining a groove and suspending the forearm of a patient in said padded body such that the forearm is positioned into the groove and the elbow of said forearm rests lightly on the base of said padded body so as to secure the forearm in the device.

BRIEF DESCRIPTION OF THE DRAWINGS

The invention is pointed out with particularity in the appended claims. The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

The claimed invention will be more completely understood through the following detailed description, which should be read in conjunction with the attached drawings. In this description, like numbers refer to similar elements within various embodiments of the present invention.

DETAILED DESCRIPTION OF THE INVENTION

Figure 1:
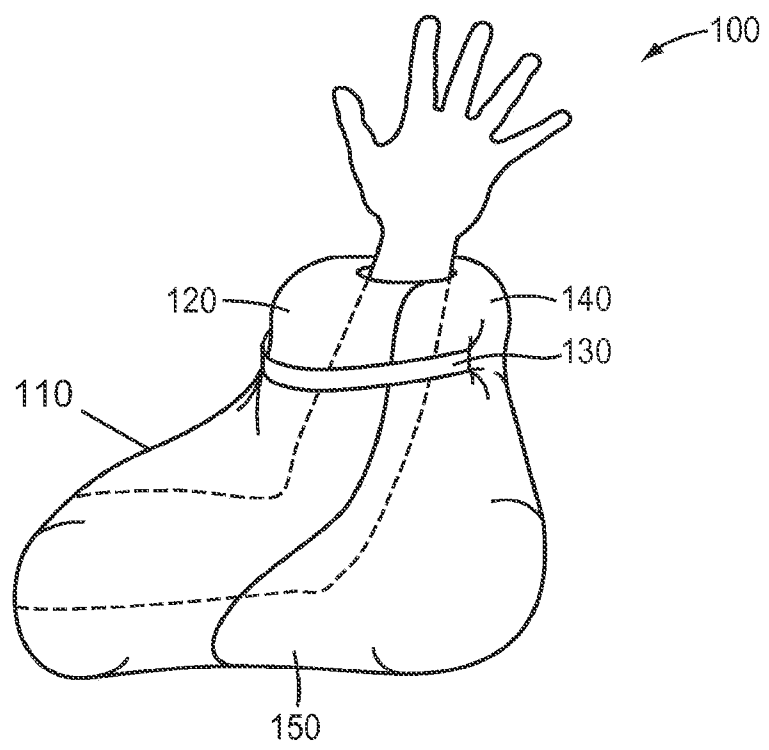
FIG. 1 depicts a front perspective view of the device with a phantom rendition of the patient's forearm positioned with the elbow in a groove of a padded body with the forearm resting against the vertical supporting region according to an illustrative embodiment of the invention.

FIG. 1 depicts a front perspective view of the device 100 that includes a padded body 110 defining a groove 120, a padded base 150 and a strap 130; shown with a phantom rendition of the patient's forearm positioned with the elbow in the groove 120 of the padded body 110 with the forearm suspended within the vertical supporting region 140 and the elbow resting on the base 150. The strap 130 is attached to the padded body 110, so that, in use, the strap 130 suspends the forearm against the vertical groove and allows the elbow to rest lightly on the base. Friction between the forearm and the material lining the groove of the device helps reduce the pressure on the on the forearm and helps keep the forearm suspended reducing the pressure on the elbow against the base.

The padded body 110 can be made of various compositions including, but not limited to, foam, memory foam, hypoallergenic material, synthetic material or inflatable material. The strap can be made of fabric or leather. The fastening mechanism of the strap 130 can be Velcro, hook and latch, a clasp, or a snap. The strap 130 can be attached to the padded body 110 via sewing, pinning, gluing, or stapling. The device may be constructed with a removable cover for easy cleaning The cover includes openings to permit the strap to exit through the cover to permit it to secure the forearm in the groove. Alternatively the groove and base may be lined with a removable liner or fabric. The removable liner may be attached to the groove and base with Velcro or snaps.

Figure 2:
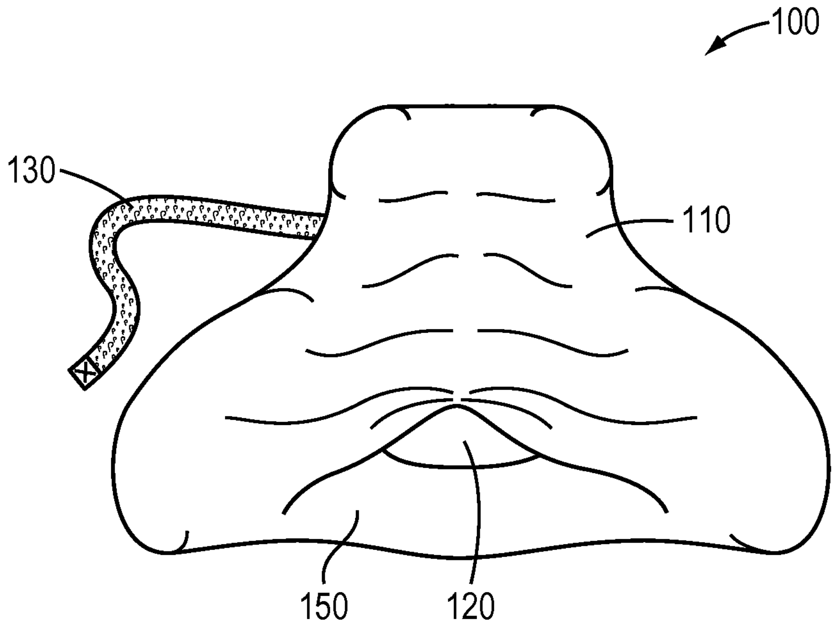
FIG. 2 depicts a front view of the device according to an illustrative embodiment of the invention.

FIG. 2 depicts a front view of the device 100 as viewed from the front that includes a padded body 110 and a strap 130. In one embodiment the shape of the base 150 is substantially triangular in shape. In other embodiments the base 150 may be U-shaped, or some other appropriate shape. In still further embodiments, the base 150 may have a flared base to prevent forward and backward or lateral rolling.

Figure 3:
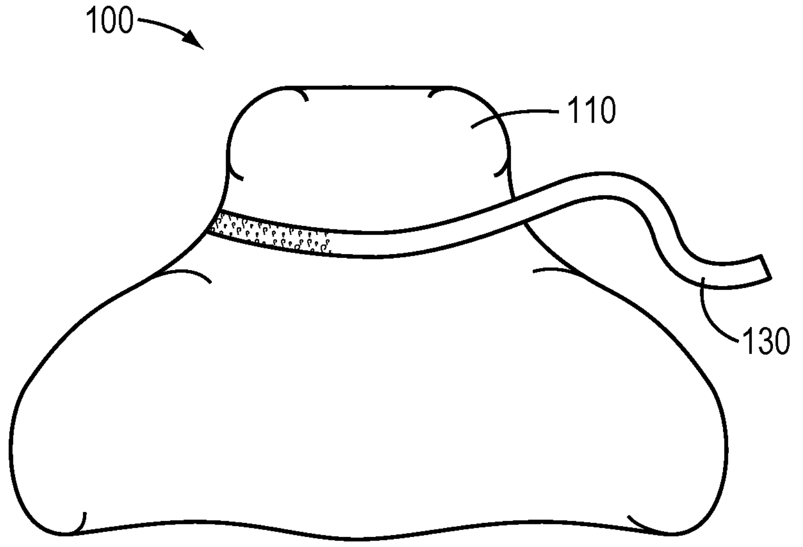
FIG. 3 depicts a back view of the device according to an illustrative embodiment of the invention.
Figure 4:
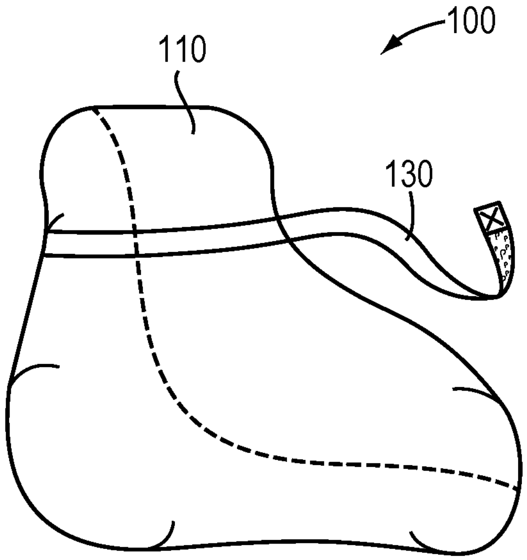
FIG. 4 depicts a side view of the device according to an illustrative embodiment of the invention.
Figure 5:
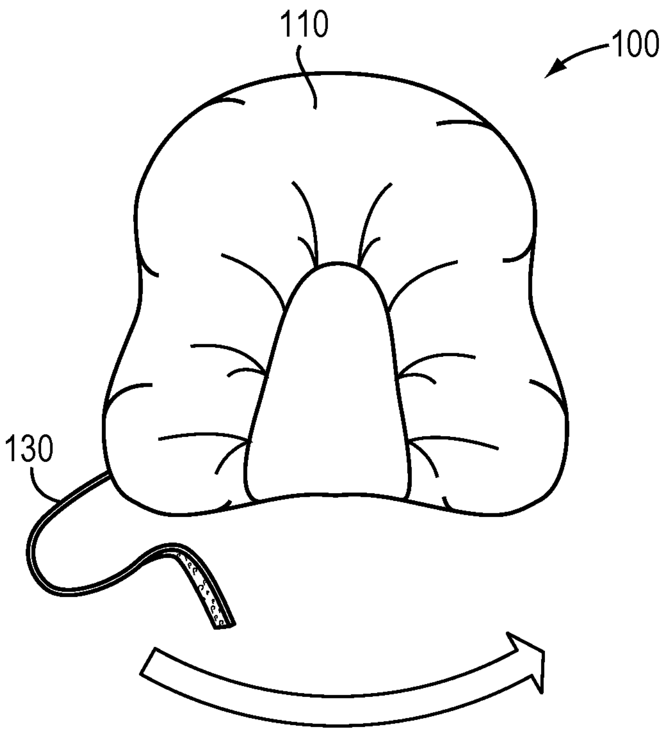
FIG. 5 depicts a top view of the device according to an illustrative embodiment of the invention.

FIG. 3 depicts a back view of the device 100 that includes a padded body 110 and a strap 130. FIG. 4 depicts a side view of the device 100 that includes a padded body 110 and a strap 130. FIG. 5 depicts a top view of the device 100 that includes a padded body 110 and a strap 130.

Figure 6:
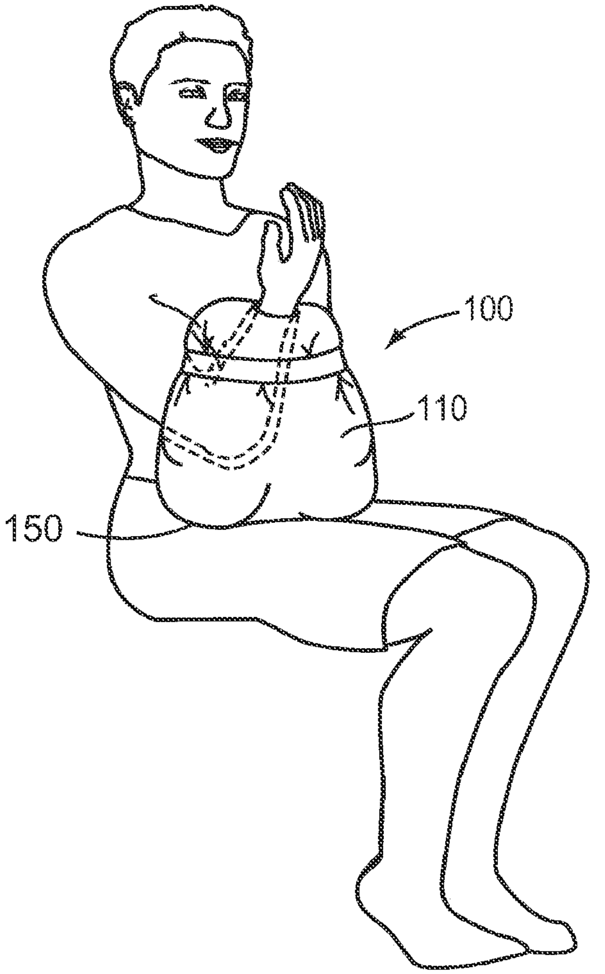
FIG. 6 depicts a side view of the device being used by a patient seated in a chair utilizing the padded body to elevate the patient's forearm and hand according to an illustrative embodiment of the invention.
Figure 7:
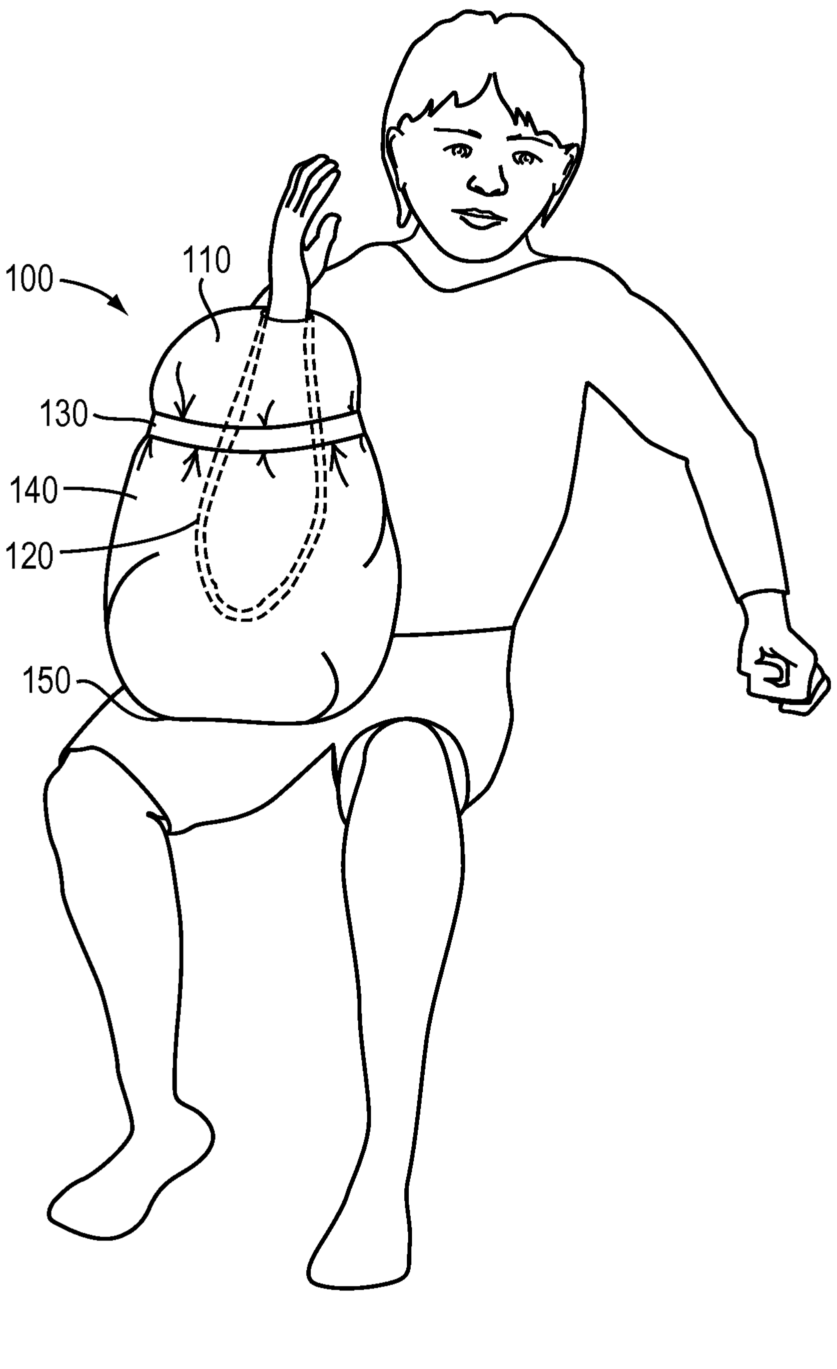
FIG. 7 depicts a front view of the device being used by a patient seated in a chair utilizing the padded body to elevate the patient's forearm and hand according to an illustrative embodiment of the invention.
Figure 8:
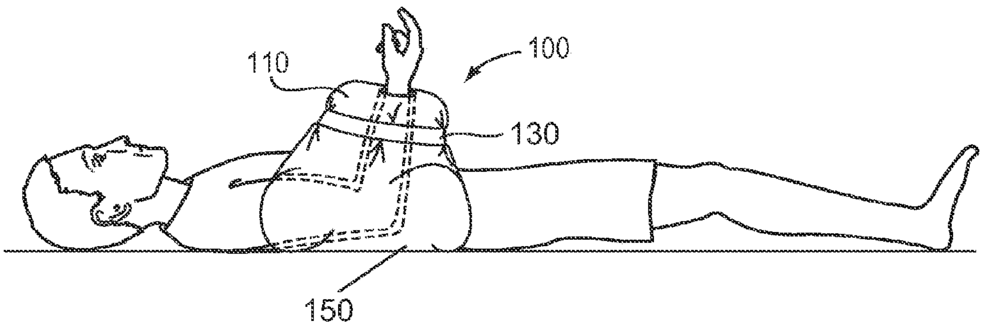
FIG. 8 depicts a side view of the device being used by a patient lying down utilizing the padded body to elevate the patient's forearm and hand according to an illustrative embodiment of the invention.

FIGS. 6 and 7 depict a device 100 being used by a patient seated in a chair utilizing the padded body 110 to immobilize and elevate the patient's forearm, with the base 150 resting on the arm of the chair. FIG. 8 depicts a side view of a device 100 being used by a patient lying down utilizing the padded body 110 to elevate the patient's forearm and hand, with the base 150 resting on a bed or other surface.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What is claimed is:

1. A device for keeping a forearm and hand of a patient elevated substantially vertically, comprising: a substantially flexible padded body having a base and a vertical supporting region defining a groove in which said forearm is maintained and supported such that the elbow of said forearm of said patient will rest lightly on the base of said substantially flexible padded body and the forearm will rest in the groove of said padded body in a vertical orientation; and a strap attached to the vertical supporting region, said strap to secure and aid in maintaining the forearm in the device, wherein an upper arm of the patient is positioned adjacent the base of the padded body;

wherein the base of the padded body provides a stable surface for maintaining the forearm and the hand of the patient in a substantially vertical orientation; and wherein the padded body envelops the forearm when the forearm is in the groove and the strap secured so that the forearm is completely cushioned about the forearm's circumference.

2. The device of claim 1, wherein the strap is comprises at least one of Velcro, fabric or leather.

3. The device of claim 1, wherein the strap is secured to the padded body by Velcro, a snap, a clasp or a hook and latch.

4. The device of claim 1, wherein the padded body is enclosed by a removable cover, said cover having at least one opening into which said padded body is inserted.

5. The device of claim 3, wherein the padded body is lined with a removable liner or fabric, said liner or fabric being secured to the padded body by Velcro, a snap, a clasp or hook and latch.

6. The device of claim 1, wherein the base is substantially triangular or U-shaped, and wherein the length of the vertical supporting region is substantially the length of the forearm of said patient.

7. The device of claim 1, wherein the base is substantially flared, and wherein the length of the vertical supporting region is substantially the length of the forearm of said patient.

8. A device for keeping a forearm and hand of a patient elevated, in substantially a vertical orientation, comprising: a padded body having a base and a vertical supporting region defining a groove in which said forearm is maintained such that the elbow of said forearm of said patient will rest lightly on the base of said padded body and the forearm will rest and be suspended in the groove of said padded body in a substantially vertical orientation, said base being substantially triangular or U-shaped and providing a surface so as to maintain the hand and forearm in a substantially vertical orientation, and said vertical supporting region being substantially the length of the forearm of said patient; and a strap attached to the vertical supporting region, said strap to secure and help maintain the forearm in the device;

wherein the padded body envelops the forearm when the forearm is in the groove and the strap secured such the forearm is completely cushioned about the forearm's circumference.

9. A method for using a device for keeping a forearm and hand of a patient elevated in a substantially vertical orientation, said method comprising the steps of: providing a padded body having a base and a vertical supporting region defining a groove; and placing and securing the forearm of a patient in said padded body such that the forearm is maintained within the groove, and the upper arm and the elbow of said forearm rests lightly on the base of said padded body so as to keep the forearm and hand in substantially a vertical orientation, wherein the padded body envelops the forearm when the forearm is in the groove and the strap secured such the forearm is completely cushioned about the forearm's circumference.

* * * * *